(12) United States Patent
Duran

(10) Patent No.: US 6,358,277 B1
(45) Date of Patent: Mar. 19, 2002

(54) ATRIO-VENTRICULAR VALVULAR DEVICE

(75) Inventor: Carlos M. G. Duran, Missoula, MT (US)

(73) Assignee: The International Heart Institute of Montana Foundation, Missoula, MT (US)

( * ) Notice: Subject to any disclaimer, the term of this patent is extended or adjusted under 35 U.S.C. 154(b) by 0 days.

(21) Appl. No.: 09/598,630

(22) Filed: Jun. 21, 2000

(51) Int. Cl.[7] ................................................. A61F 2/24

(52) U.S. Cl. .................. 623/2.12; 623/2.13; 623/23.72; 623/2.11

(58) Field of Search .............................. 623/2.12, 2.13, 623/2.36, 23.72, 2.16

(56) References Cited

U.S. PATENT DOCUMENTS

| | | | | |
|---|---|---|---|---|
| 3,739,402 A | * | 6/1973 | Cooley et al. | 623/2.16 |
| 4,790,844 A | * | 12/1988 | Ovil | 623/2.13 |
| 4,960,424 A | * | 10/1990 | Grooters | 623/2.13 |
| 5,156,621 A | * | 10/1992 | Navia et al. | 623/2.12 |
| 5,344,442 A | * | 9/1994 | Deac | 623/2.12 |
| 5,415,667 A | | 5/1995 | Frater | 623/2 |
| 5,500,015 A | | 3/1996 | Deac | 623/2 |
| 5,733,331 A | * | 3/1998 | Peredo | 623/2.13 |
| 5,824,067 A | * | 10/1998 | Gross | 623/2.16 |
| 6,214,055 B1 | * | 4/2001 | Simionescu et al. | 623/23.72 |

FOREIGN PATENT DOCUMENTS

WO 99/66967 12/1999 ........... A61L/27/00

OTHER PUBLICATIONS

Mickleborough et al., "A Simplified Concept for a Bileaflet Atrioventricular Valve that Maintains Annular–Papillary Muscle Continuity", Journal Cardiac Surgery 1989;4:58–68.

Deac et al., "New Evolution in Mitral Physiology and Surgery: Mitral Stentless Pericardial Valve", Annals Thoracic Surgery 1995; 60:S433–8.

Liao et al, "Intraoperative Epicardial Echo/Doppler Evaluation of a Stentless, Chordally Supported Quadricusp Miltral Bioprosthesis", ASAIO Journal 1993; 39:M634–8.

(List continued on next page.)

*Primary Examiner*—David H. Willse
*Assistant Examiner*—Suzette J. Jackson
(74) *Attorney, Agent, or Firm*—Klein & Szekeres LLP

(57) ABSTRACT

An anatomically designed atrioventricular valve is made of biologically compatible synthetic membrane or biological membrane of autologous, homologous or heterologous origin. A single piece of the selected membrane material is trimmed so as to form two unequal sheaths similar to the normal anterior and posterior mammalian mitral valve leaflets with a wide upper base to be sutured to the host's mitral annulus. These two leaflets are prolonged and tapered into two thin bands to be connected to the papillary muscles serving as replacements for the natural marginal chordae tendinae of the normal mitral valve. The two lateral sides of the membrane are joined to form a truncated cone with a wider upper circular base and a narrow extremity formed by the thin chordal bands. A set of sutures are placed between selected points at the base of the cone and the two thin prolongations serving as replacements for the strut or stay basal chords of the natural mitral valve. Thus, the mitral valve prosthesis is anatomical because it is stentless, bicuspid and supported by marginal and basal chordae. Obturators and sizers in the configuration of rods of varying diameter, to measure the host's valve annulus diameter and select the appropriate size of the prosthesis are used during implantation of the prosthesis. A rod shaped holder maintains the prosthesis during implantation, and a curved bodied measuring instrument is used to determine the precise location where the chordae tendinae of the prosthesis are to be sutured to the papillary muscles of a recipient mammal.

18 Claims, 8 Drawing Sheets

OTHER PUBLICATIONS

Miki et al., "Mitral Valve Replacement with Preservation of Chordae Tendineae and Papillary Muscles", Annals Thoracic Surgery 1988; 45:28–34.

Duran, "Perspectives in Reparative Surgery for Acquired Valvular Disease", Advances in Cardiac Surgery, 1993; 4:1–23.

Doty et al., "Mitral Valve Replacement with Homograft", Annals Thoracic Surgery 1998; 66:2127–31.

Duran, "Mitral Valve Allografs. An opportunity", J. Heart Valve Disease; 1995; 4:29–30.

Van der Spuy, "Completely Anatomical Autogenous Whole Mitral Valve", Thorax 1964; 19:526–29.

Holdefer, et al., "An Experimental Approach to Mitral Valve Replacement with Autologous Pericardium", Journal of Thoracic & Cardiovascular Surgery 1968; 55:873–81.

* cited by examiner

ATRIO-VENTRICULAR VALVULAR DEVICE

BACKGROUND OF THE INVENTION

1. Field of the Invention

The present invention is in the field of heart valve prostheses. More specifically, the present invention is directed to the replacement of the atrioventricular valves with an anatomically designed mitral valve. The present invention is also directed to obturators and sizers to measure the host's valve annulus diameter and select the appropriate size of the prosthesis, to a holder to maintain the prosthesis during implantation, and to a measuring instrument to determine the locations for suturing parts of the prosthesis to the papillary muscles of the patient.

2. Brief Description of Background Art

Replacement of the diseased heart valves is a frequent operation in cardiac surgery. As is known, heart valves (aortic, pulmonary, mitral and tricuspid) function essentially as check valves operating hemodynamically in synchronization with the pumping action of the heart, allowing blood to flow in a downstream direction and blocking flow in the opposite or upstream direction. In disease, this function is impaired either through narrowing of the valve or regurgitation. The natural heart valves are of two distinct basic configurations. The sigmoid valves (aortic and pulmonary valves) are situated on the outflow of the left and right ventricles and are made of three small and similar cusps inserted into the base of the aorta or pulmonary trunk. The atrioventricular valves (mitral and tricuspid valves) consist of several large leaflets of different size attached at their base to the valve annulus and held at their free edge with a complex variety of tendons called chordae tendinae that are inserted into the papillary muscles of the ventricles.

The chordae tendinae are of two main types: those extending from the papillary muscles to the free edge or margin of the leaflets are called "marginal chords" and those extending from the papillary muscles to the undersurface or ventricular surface of the leaflets are called "basal chords." Among these basal chords, two thicker chords are attached to each papillary muscle and to the undersurface of the anterior mitral leaflet close to its base in the mitral annulus. These chords have been labeled "principal," "strut," or "stay" chords. The marginal and basal cords serve different functions. The marginal chords are essential for the competence of the atrioventricular valves. During diastole the valve is open to allow for the passage of blood, the leaflets are separated and the marginal chords are slack. During systole, the pressure in the ventricle closes the valve by bringing the leaflets together. The marginal chords become taut to maintain the leaflets in contact. In a diseased heart rupture or elongation of the marginal chords results in prolapse of the leaflets towards the atrium and consequently, valve insufficiency. The basal chords hold the body of the leaflets during systole, and the strut chords remain taut during the whole cardiac cycle and fulfill the function of maintaining the overall geometry of the ventricles.

The above-described functions of the chordae tendinae were ignored until recently as far as atrioventricular valve replacement was concerned. In surgery, when a diseased atrioventricular valve needed replacement, the whole mitral apparatus was excised including the leaflets and marginal and basal chords. However, recent experimental and clinical observations have shown that maintaining the continuity or attachment between the papillary muscles and the mitral annulus is essential to preserving the pumping action of the ventricles (Miki et al. Mitral Valve Replacement with Preservation of Chordae Tendinae and Papillary Muscles. Annals Thoracic Surgery 1998;45:28–34). Therefore, relatively recently the art has recognized the need to maintain annulo-papillary continuity when replacing an atrioventricular valve, but attempts to do so have met less than full success.

Proximally, the valve leaflets are attached to the annulus. This structure is not rigid and changes in shape continuously during the cardiac cycle. During diastole the atrioventricular annulus becomes circular and therefore of the largest possible diameter to allow maximum blood flow. During systole, the annulus area is significantly reduced, becoming smaller and "D" shaped, and facilitating the apposition of the valve leaflets. In this description of the prior art and ensuing description of the invention the terms "proximal", "distal" "anterior" and "posterior" are used in the anatomical sense. "Proximal" means "upstream" as far as blood flow is concerned, "distal" means downstream; "anterior" means closer to the sternum, and "posterior" means closer to the spine.

Restoration to normal function while maintaining whole the atrioventricular valves is sometimes possible with specific repair techniques (Duran Perspectives in Reparative Surgery for Acquired Valvular Disease. Advances in Cardiac Surgery, 1993;4:1–23). Although the results of this surgery have been shown to be superior to valve replacement, the distortion of the valve often makes its replacement imperative. The standard replacement of the mitral and tricuspid valves is with either mechanical or bioprosthesis. All these prior art prostheses are not anatomical, i.e. they do not reproduce the normal atrioventricular valves. Usually, a single design is used for all positions, be it sigmoid or atrioventricular. The mechanical valves used for replacement resemble neither the sigmoid nor the atrio-ventricular valves.

The commercially available bio-prostheses are porcine or pericardial aortic valves. The prostheses used for mitral or tricuspid replacement are in fact aortic prostheses differing only in their sewing ring, not in the actual valve mechanism. Furthermore, both the mechanical and the bio-prosthesis are mounted on a rigid casing that does not allow for the normal changes in shape and size of the atrioventricular annulus. This rigidity of the annulus of the replacement valves of the prior art has been shown to reduce the efficiency of ventricular function. Because the mitral valve is subjected to much higher pressure and stress and has a lower flow velocity than the other heart valves, its prosthetic replacement carries the worst clinical results and prognosis in terms of durability and thromboembolism.

The only anatomically designed mitral valve used clinically is the mitral homograft. In this case, the whole mitral valve apparatus from a cadaver is transplanted into the recipient (Doty, et al. Mitral Valve Replacement with Homograft. Annals Thoracic Surgery 1998;66:2127–31 and Duran, Mitral Valve Allografts. An opportunity. J Heart Valve Disease;1995:4:29–30). This procedure is technically difficult, and its results are still controversial. Probably, there are not more than 200 cases worldwide.

More closely anatomically designed mitral valves made of pericardium have also been designed and tested, mostly experimentally, in the prior art. In 1964 Van der Spuy (Completely Anatomical Autogenous Whole Mitral Valve. Thorax 1964; 19:526–29) described a mitral valve prosthesis made of two pairs of pieces of pericardium shaped as two large anterior and two smaller posterior leaflets. Several strips of ilio-tibial ligament were sutured to the leaflets (sandwiched between each pair of leaflets) and the other extremities tied together into two bundles which were anchored to the papillary muscles. A semicircular length of thick nylon thread was sutured around the upper margin of the anterior and posterior leaflets to provide stability to the valve. The author implanted this valve in two patients; one died 10 hours after surgery and the other was reported alive 6 weeks after implantation. No further information on this technique is available.

In 1968 Holdefer, et al. described two designs of a mitral valve made of autologous pericardium. (An Experimental Approach to Mitral Valve Replacement with Autologous Pericardium. Journal of Thoracic & Cardiovascular Surgery 1968;55:873–81) In the first design, two separate pieces of pericardium were trimmed to reproduce the anterior and posterior mitral leaflets with their base to be sutured to the mitral annulus. The free edges of the two leaflets were trimmed into two strips for each leaflet to represent the chords. These chords were attached to the controlateral papillary muscle in an X configuration. In the second design, preferred by the authors, two similar crescent shaped leaflets were supported by the two pericardial chords attached to a long suture that was passed through the papillary muscles and left ventricular wall and brought into the left atrium close to the mitral annulus. The idea was to control the correct length of the chords from the atrium by observing the leaflet closure. The authors reported a maximum survival of 28 days in one out of 34 calves.

In 1989 Mickleborough et al. described a mitral valve made of a rectangle of bovine pericardium wrapped around a rod and sutured to form a cylinder. (A Simplified Concept for a Bileaflet Atrioventricular Valve that Maintains Annular-Papillary Muscle Continuity. Journal Cardiac Surgery 1989;4:58–68.) In this device two triangular portions of the pericardium are removed leaving two wide strips of pericardium to be sutured to the papillary muscles. To the present inventor's knowledge, this valve has never been implanted in patients.

U.S. Pat. No. 5,344,442 and an article by Deac et al. described in 1995, a design very similar to that of Mickleborough et al. (New Evolution in Mitral Physiology and Surgery: Mitral Stentless Pericardial Valve. Annals Thoracic Surgery 1995;60:S433–8.) Two trapezoidal pieces of pericardium are sutured together to form an inverted cone with an upper or proximal circumference to be sutured to the patient's mitral orifice. At the other extremity of the cone, two semicircular portions of the pericardium are excised resulting in extensions that are to be sutured to the two papillary muscles. Three different valve sizes are described in this design to accommodate the varying diameters of the mitral orifices of the different patients. The author has reported favorable results in about 30 patients operated in Rumania.

U.S. Pat. No. 5,415,667 and Liao et al. describe a quadricuspid mitral prosthesis made of bovine pericardium (Intraoperative Epicardial Echo/Doppler Evaluation of a Stentless, Chordally Supported Quadricuspid Mitral Bioprosthesis. ASAIO Journal 1993;39:M634–8). A large anterior, a smaller posterior and two even smaller "commissural" leaflets are sutured together to form a square-shaped proximal orifice to be sutured to the patient's mitral annulus. The distal extremities of the four leaflets are slit and fashioned into six bands of the same material that are sutured together into two strips that serve as chords and are anchored to both papillary muscles. The valve is mounted on a temporary stent to simplify its insertion. This bioprosthesis is under clinical trials.

The foregoing review of the previous art shows that the design of mitral valve prostheses has lagged behind the large number of aortic valve prostheses designed in the last three decades. This is perhaps because the geometry of the natural mitral valve is far more complex than the geometry of the sigmoid valves. The above-described five known mitral valve designs of the prior art have the common feature that they are stentless. Also, all of them have a proximal circular orifice that is sutured to the patient's mitral orifice.

However, these known prior art designs have significant differences in the distal or chordal apparatus that should correspond to the natural chordal system to be attached to the papillary muscles. Mickleborough's and Deac's models are basically a cylinder or a cone having its lower or distal part slightly trimmed down. Primarily designed for construction at the time of surgery, these two models are simple but they are far from resembling the natural valve. Holdefer and Frater's designs have pericardial chords in continuity with the leaflets and are therefore structurally stronger than the separate tissue chords of Van der Spuy's model. Holdefer's and Van der Spuy's models are rather complex and in Holdefer's design, the chordal implantation technique is difficult and unreliable. Frater's design is a quadrilateral valve. It represents an attempt at being as close as possible to the normal valve, which in fact has six scallops (one anterior, two commissural and three posterior). However, none of the above described valves have basal chords, which as noted above, are a constitutive part of the natural mitral apparatus and are essential for the systolic function and proper geometry of the ventricle.

SUMMARY OF THE INVENTION

In accordance with the present invention, a mitral valve prosthesis comprises a single unitary member that forms two leaflets. The prosthesis is made of a flexible membrane of biocompatible synthetic or autologous, homologous or heterologous tissue. To form the prosthesis a rectangle of this membrane is trimmed so that two substantially trapezoidal flaps of different size and shape result. The membrane flaps are configured for the larger flap to form an anterior leaflet and for the smaller flap to form a posterior leaflet of the mitral valve. In the prosthesis the two lateral sides of the above formed membrane are joined together with a suture to form substantially an inverted truncated cone having a circular non-supported larger base that is to be sutured to the patient's valve annulus, and a smaller base consisting of two narrow bands that undertake the function of the marginal chordae tendinae of the mitral valve. The suture of the lateral sides of the membrane can correspond to the junction of the anterior and posterior leaflets or to the center of the posterior leaflet. The extremity of the two tissue chords is reinforced with a Teflon, Dacron or like synthetic pledget or by folding the extremity of the membrane on itself. Two strut chords made of biological or non-absorbable synthetic suture-like material extend between the base of the prosthesis and the extremity of both chordal bands. The length of these strut chords is inferior to the maximum length of the membrane between the prosthesis base or annulus and the extremity of the membrane chords. For this reason the total height of the truncated cone cannot be stretched completely because it is limited by the shorter length of the strut chords.

A set or series of obturators are also provided for use during implantation of the mitral valve prosthesis of the invention. The obturators are plastics rods of varying diameters, and have a rounded end (to avoid damage to the patient's tissues) and a flat end. Conspicuous marking identifies the diameter of each obturator.

During implantation an obturator one size below the size of the prosthesis (as determined by the sizer) is introduced through the prosthesis after the prosthesis is in place, and the membrane chords have been sutured to the papillary muscles and the prosthesis annulus has been sutured to the mitral annulus but not tied. These sutures are then tied with the obturator in place. This avoids constricting the annulus of the patient and of the prosthesis which are not fixed by any rigid structure.

A holder for the mitral prosthesis of the present invention is also provided to maintain the prosthesis in place during its implantation. The holder is essentially a plastic cylinder of a diameter slightly smaller than the diameter of the mitral prosthesis. One end of the cylinder is tapered into a smaller diameter to serve as handle for the surgeon and the other end of the cylinder is flat. The mitral prosthesis is introduced through the holder and placed so that the extremities of the chordal bands protrude beyond the end of the holder. The mitral prosthesis is held to the holder by a band or bands to be removed when the holder is removed.

An instrument comprising a convoluted loop of wire, or a body of like configuration, is provided to determine the proper points of attachment by sutures of the strut cords to the chordal strips, and of the chordal strips to the papillary muscles.

The relative sizes of all the components of the prosthesis are related to each other so that a series of different size prostheses are available. The appropriate prosthesis size is determined by the patient's mitral annulus. The anatomically correct mitral prosthesis of the present invention is stentless, and is bileaflet in appearance, but when closed under ventricular pressure, it takes the appearance of one anterior and three posterior scallops. The chords are in continuity with the leaflets and readily sutured to the homolateral papillary muscle because of their thick extremity. The invention overcomes a major surgical problem in mitral repair, mitral homograft replacement and anatomic mitral valve prosthesis implantation which is to determine the location in the papillary muscle where the chords are to be sutured for correct tension. In accordance with the present invention, the basal chords stretch between the extremity of the two chords and the base of the leaflets. This distance is shorter than the length between the leaflet bases and the extremity of the chords. At implantation, once the basal chords are taut, they do not allow the marginal chords to be sutured beyond their correct distance.

BRIEF DESCRIPTION OF THE DRAWING FIGURES

DESCRIPTION OF THE PREFERRED EMBODIMENTS

The following specification, taken in conjunction with the drawings, sets forth the preferred embodiments of the present invention. The embodiments of the invention disclosed herein are the best modes contemplated by the inventor for carrying out his invention in a commercial environment, although it should be understood that various modifications can be accomplished within the parameters of the present invention.

Figure 1:
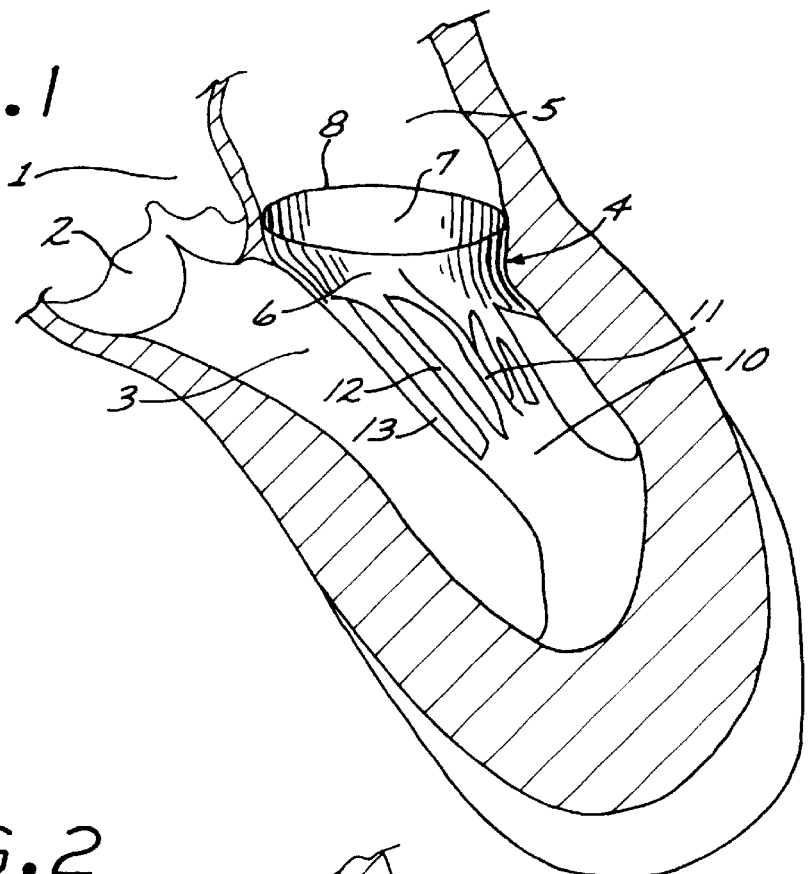
FIG. 1 is a schematic diagram, partly in cross-section, of the left heart cavities of a mammal showing the natural mitral valve, the valve annulus, leaflets and chordae tendinae.

Referring now to the drawing figures, FIG. 1 is a schematic diagram of a longitudinal section of the normal heart showing the aorta 1, aortic valve 2, left ventricle 3, mitral valve 4 and left atrium 5. The mitral valve 4 permits the unidirectional flow of the oxigenated blood from the left atrium 5 into the left ventricle 3. The aortic valve 2 permits the unidirectional flow of blood from the left ventricle 3 to the aorta 1. The natural mitral valve 4 has two main leaflets; a larger anterior mitral leaflet 6 and a smaller posterior leaflet 7. The bases of the leaflets 6 and 7 are attached to the mitral annulus 8 while the leaflet's free edge is held by the chordae tendinae, which are attached to the papillary muscles 10. The chordae tendinae include the marginal chords 11 which are attached to the free edges of the leaflets 6 and 7 and are taut during systole, maintaining the leaflets in contact. The chordae tendinae include the basal chords 12 which extend from the papillary muscles 10 to the ventricular surface of the anterior and posterior leaflets 6 and 7. The basal cords include the strut or stay chords 13 which are two particularly thick basal chords that stretch from the papillary muscles 10 to the undersurface of the anterior leaflet 6 but also reach the annulus 8. These strut chords are taut during the whole cardiac cycle, playing an essential role in maintaining the normal geometry of the left ventricle 3. With respect to the drawing figures it should be noted that their purpose is to illustrate the valve prosthesis of the present invention and the manner of using it. It is not their purpose to provide absolutely accurate anatomical depiction of the heart. This is indicated by the frequent reference to the fact that the drawings are "schematic" or diagrams only.

Figure 2:
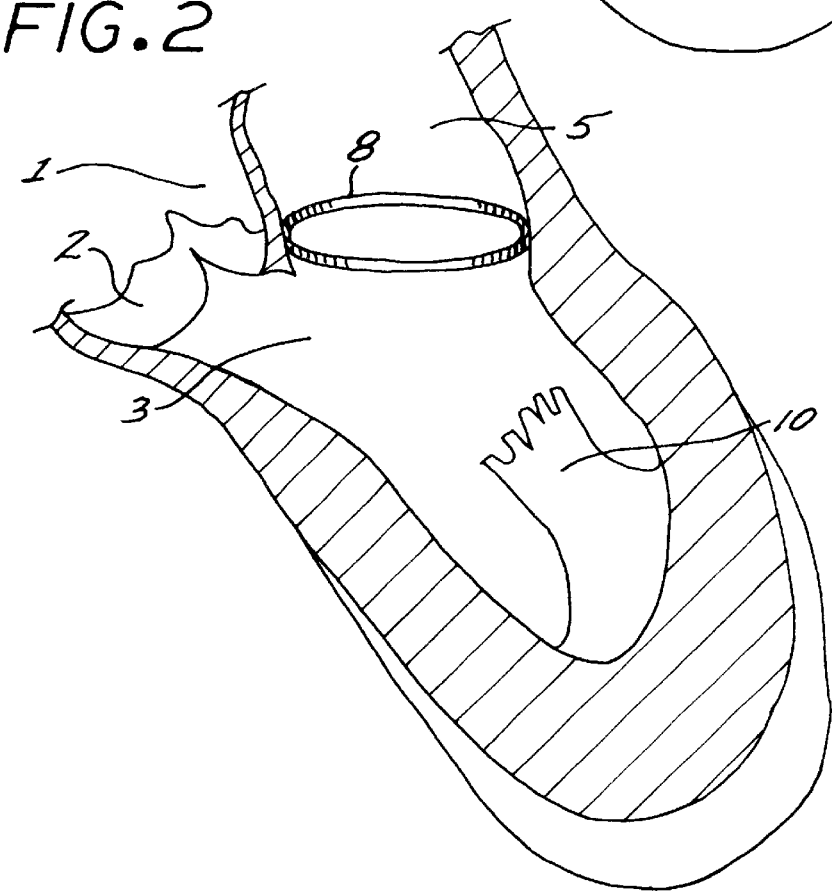
FIG. 2 is a schematic diagram, partly in cross-section, of the left heart cavities of the heart after excision of the mitral valve apparatus showing the mitral annulus and papillary muscles.

FIG. 2 is a schematic diagram of the left heart cavities after surgical excision of the whole mitral apparatus. After this operation only the mitral annulus 8 and the papillary muscles 10 remain and are shown in this figure. The leaflets and chordae tendinae have been resected. A mitral valve replacement with a mitral prosthesis is required.

Figure 3:
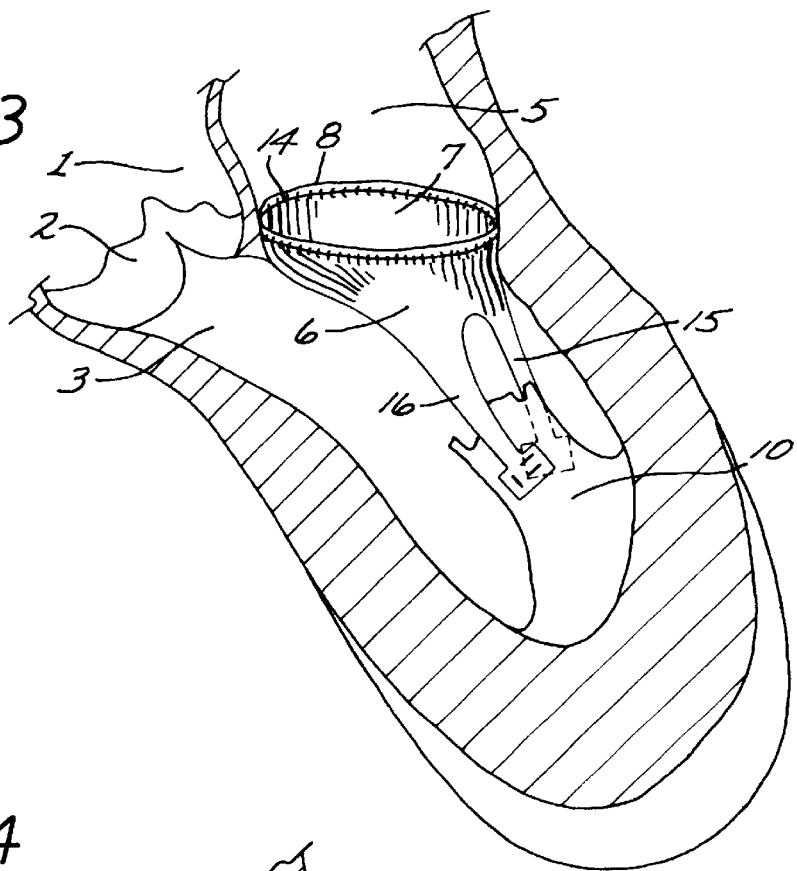
FIG. 3 is a schematic diagram, partly in cross-section, of the left heart cavities with a view of the mitral valve replaced with a stentless mitral valve similar to the valve of the present invention but without strut chords.

FIG. 3 is a schematic diagram showing the left heart cavities 3 and 5 after replacement of the natural mitral valve 4 with a pericardial stentless prosthesis. This prosthesis may be somewhat similar in configuration to the prosthesis of the invention and has an anterior 6 and a posterior 7 leaflet anchored to the mitral annulus 8 with a suture 14 and two strips or chordal bands 15 and 16 of the same material (pericardium) sutured to the papillary muscles 10. An important difference from the present invention is that this design ignores the importance of the basal chords, and has no replacement or equivalent to the natural strut cords that are shown as 13 in FIG. 1. Therefore, the left ventricle 3 is left unsupported.

Figure 4:
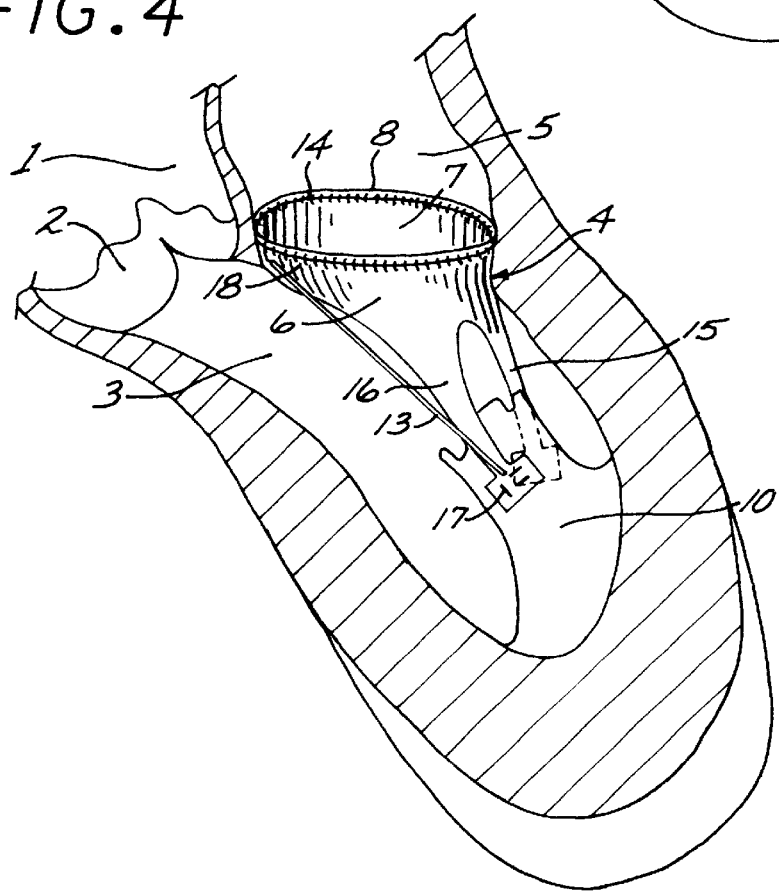
FIG. 4 is a schematic diagram, partly in cross-section, of the left heart cavities showing the mitral valve of the invention including strut chords.

FIG. 4 is a schematic view, similar to FIGS. 1, 2 and 3, showing the mitral valve 4 of the present invention in place. The bases of the anterior 6 and posterior 7 leaflets have been sutured 14 to the host's mitral annulus 8, and the two chordal bands 15 and 16 have been attached by suture 17 to the papillary muscles 10. One of two strut chords 13 is shown stretching from the extremity of one of the two chords 16 to the anterior portion of the annulus or base 18 of the prosthesis.

Figure 5:
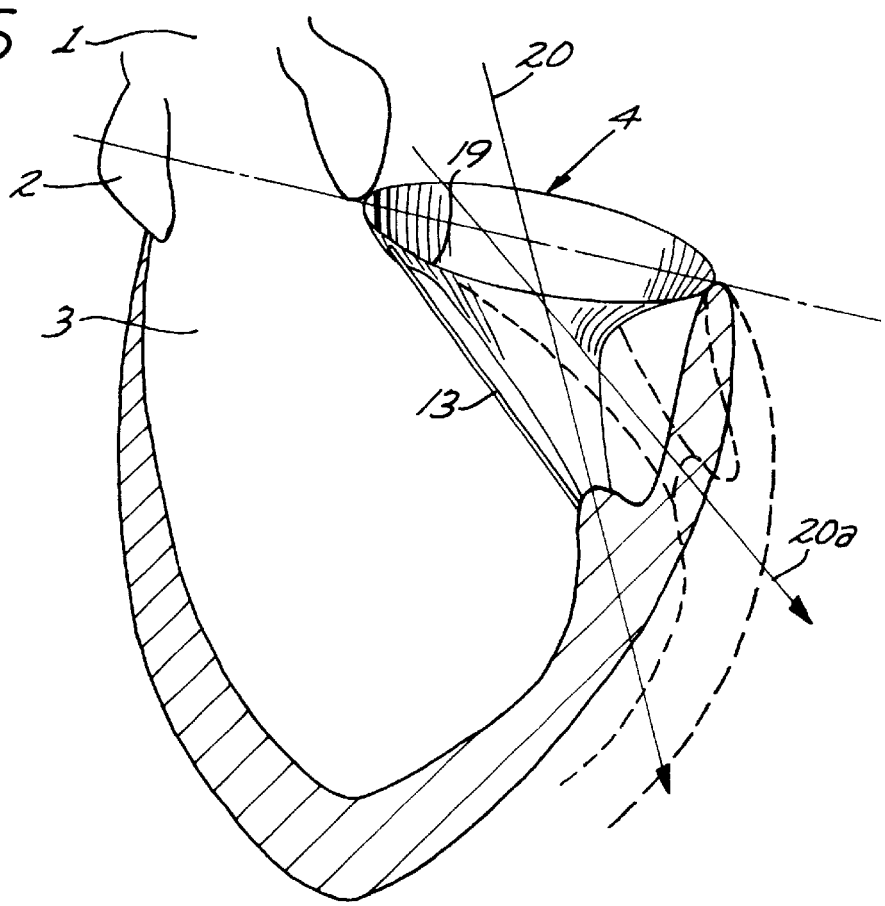
FIG. 5 is a schematic diagram, partly in cross-section, of the left ventricle showing with dotted lines the loss of geometry when a mitral prosthesis without strut chords is implanted.

The schematic view of FIG. 5 shows the aorta 1 and the aortic valve 2 open and the natural mitral valve 4 closed during systole. In a normal mitral valve 4, because of the presence of the strut chords 13, the left ventricular wall 19 is supported, maintaining the normal geometry of the ventricle 3, as shown in solid lines and by the direction of the apico-basal arrow 20. In a diseased state without functioning strut cords 13, or in case of a mitral valve prosthesis that lacks strut cords, the left ventricular wall 19 is not supported and is displaced laterally as shown by the direction of the apico-basal arrow 20a. The unsupported left ventricular wall is shown by dotted lines.

Figure 6:
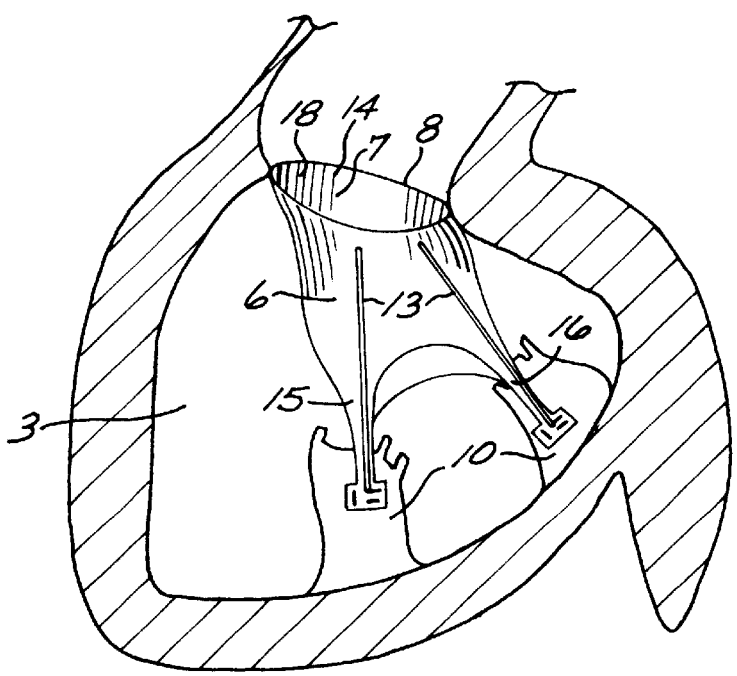
FIG. 6 is a schematic diagram, partly in cross-section, of an opened left ventricle showing the mitral valve prosthesis of the present invention implanted in place.

FIG. 6 is a schematic view showing the left ventricle 3 open with its anterior wall laterally displaced to the right. The view shows both papillary muscles 10. The mitral valve prosthesis of the present invention is inserted into this left ventricle 3. The view discloses the anterior 6 and a posterior 7 flaps, or leaflets of the prosthesis and the suture 14 that attaches the base 18 of the prosthesis to the mitral annulus 8 of the patient. This view also shows the leaflets 6 and 7 tapering into two chordal strips 15 and 16 and that these are sutured to the anterior and posterior papillary muscles 10. The hitherto described components or parts of the prosthesis comprise one single, unitary piece made from a biologically acceptable membrane, as described below. The view also shows two strut chords 13 extending from the extremity of the chordal strips 15 and 16 to the base of the anterior leaflet 6 close to the anterior portion of the mitral annulus 8. In this fashion, the physical continuity between the papillary muscles 10 and the mitral annulus 8 is maintained, ensuring the correct geometry of the left ventricle 3.

The mitral valve prosthesis of the present invention can be constructed from flexible biocompatible synthetic materials such as polyurethane, or biological material such as pericardium, pleura, peritoneum or gut submucosa. These biological membranes can be of autologous, homologous or heterologous origin and treated with state-of-the-art chemical or physical methods, or by such methods of tissue treatment that may be developed in future. In the preferred embodiment, the mitral valve prosthesis of the present invention is made from either autologous or heterologous pericardium treated with glutaraldehyde, as well known in the art. Alternatively the prosthesis can be made from pericardium or other biological membrane treated with alcohol (or like solvent) in the manner described in published PCT application WO 99/66967, published on Dec. 29, 2000, incorporated herein by reference.

Figure 7:
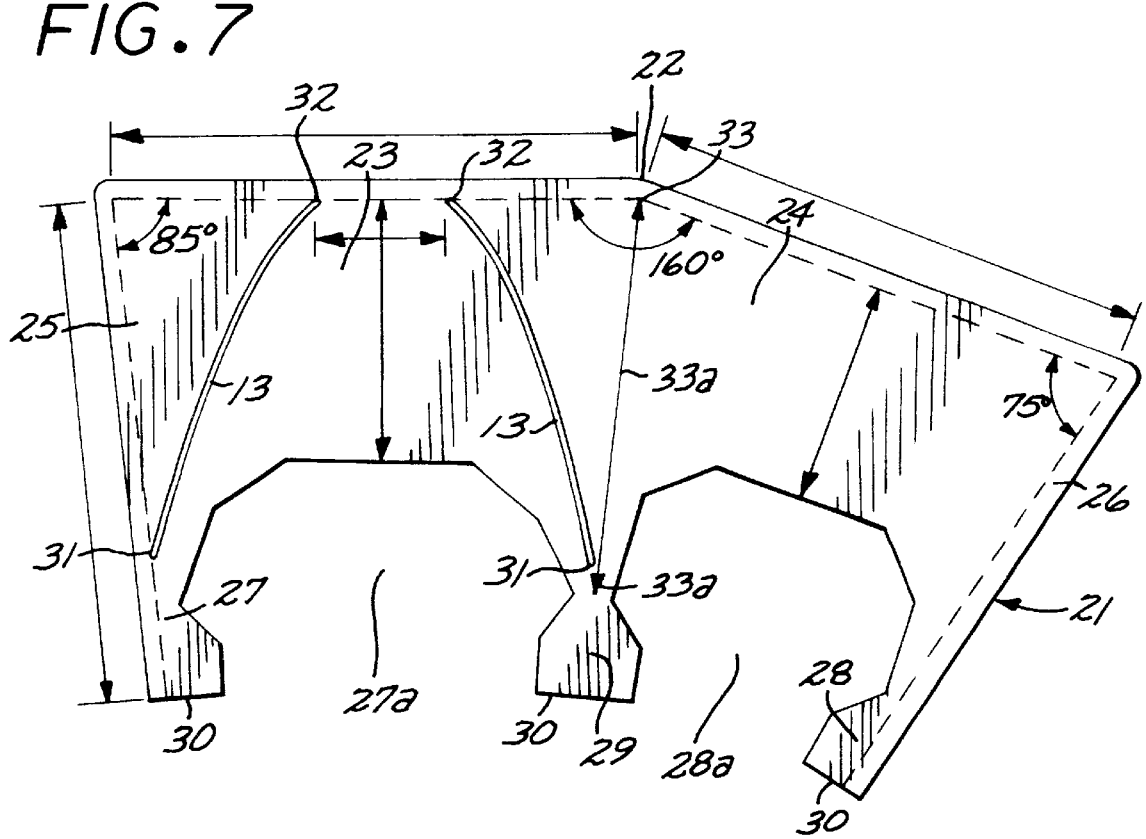
FIG. 7 is a top view of the first preferred embodiment of the template used to construct the mitral prosthesis of the present invention from biocompatible synthetic or biological membrane.

FIG. 7 discloses a template 21 used to construct the first preferred embodiment of the anatomical and stentless mitral prosthesis of the present invention. A rectangular piece of synthetic or biological membrane is placed over the template and the membrane, not shown in this figure, is trimmed to the size and shape defined by the template 21. A variety of different template sizes are made in accordance with the invention to conform the size of the prosthesis to the patient's mitral orifice. Although the template 21 is one piece it can be conceptually divided into two main flaps that correspond to the anterior 6 and posterior 7 mitral leaflets. The overall base 22 of the template 21 corresponds to the base 18 of the anterior 6 and posterior 7 leaflets of the prosthesis. Thus, this base 22 is divided into two parts 23 and 24 corresponding to the bases of the anterior and posterior leaflets. These two bases 23 and 24 are at an approximate angle of 160° to one another. The height of the prosthesis corresponds to the two equilateral sides 25 and 26 of the template 21. The angle between the lateral side 25 (corresponding to the anterior leaflet 6) and the base 23 is approximately 85°. The angle between the lateral side 26 (corresponding to the posterior leaflet 7) and the base 24 is approximately 75°. It should be understood that purpose of the template 21 is to allow the shaping of a biologically acceptable membrane to form the anatomically correct mitral valves prosthesis of the invention. The herein described parameters in terms of dimensions and angles are presently considered optimal to accomplish this purpose. However, variations and modifications of these parameters are possible and are within the scope of the invention as long as the resulting mitral valve prosthesis is substantially anatomically correct.

After the membrane (not shown in FIG. 7) has been trimmed, the two sides 25 and 26 are sutured together. Suturing per se is well-known in the art. In the preferred embodiment, 4/0 polypropylene sutures are used. The joining of the lateral sides 25 and 26 with suture forms a truncated cone with its wider base 18 defined by the base 22 of the template 21, and which corresponds to the mitral orifice of the patient. The lower or apical portion of the template includes extensions 27 and 28 which can be best described by visualizing two essentially semicircular cut-out portions 27a and 28a. In the prosthesis the extensions 27 and 28 correspond to the free edges of the anterior 6 and posterior 7 flaps or leaflets. Due to the shape of the template 21 the heights of the leaflets 6 and 7 in the resulting valve prosthesis are not equal. The height of anterior leaflet 6 is larger than the height of the posterior leaflet 7. Between the two cut out semicircular parts 27a and 28a, there is a pillar-like extension 29 that in the trimmed membrane corresponds to one chordal strip 15. The two lateral sides 25 and 26 of the template 21, one corresponding to the anterior leaflet 6, and the other to the posterior leaflet 7, form the second chordal strip 16. The ends 30 of the template material which correspond to the chordal strips 15 and 16 are widened in order to form widenings in the membrane for suturing to the patient's papillary muscles 10. The two strut chords 13 used in the mitral valve of the invention are not part of the template 21 but are nevertheless shown in FIG. 7, superimposed on the template 21.

In the preferred embodiment, the strut chords 13 are made of double ended 3/0 polypropylene or PTFE (Gore-tex). These strut chords 13 extend from points 31 at the origin of the chordal strips 15 and 16 to points 32 in the mid-third of the base 23 of the anterior leaflet 6. These locations are well demonstrated on FIG. 7 that shows the template 21. In the mitral valve the double-ended sutures are passed through the chordal bands 15 and 16 tied, passed through the base of the anterior leaflet 6, and tied. The distance between the two points 32 where the strut chords 13 are attached, respectively, to the base 23 corresponding to the anterior leaflet 6 is approximately 0.4 mm times the diameter of the prosthesis (0.4×D). The two strut chords 13 are of equal length and are approximately 1.08 mm times the diameter of the prosthesis (1.08×D). The distance between a mid-point 33 at the base of the prosthesis to a point 33a at the junction of the anterior 6 and posterior 7 leaflets is called "commissural height", indicated on the template by the arrow 33a. The length of each strut chord 13 is shorter than the "commissural height" 33a, and therefore in the resulting valve prosthesis the strut cords 13 naturally curve the anterior leaflet 6. The extremities of the two chordal strips 15 and 16 extend for a distance of approximately 12 mm beyond the point of attachment 31 of the strut chords 15 and 16. Again, this is best illustrated in FIG. 7, showing the template. Distally from the points 31 the chordal strips 15 and 16 widen to form a square of approximately 10 mm per side. In the preferred embodiment of the invention, a matching sized square of Teflon felt 34 is attached to the square at the extremity of the chordal strips with several 5/0 polypropylene sutures. The template 21 described above is an essentially flat surface in the preferred embodiment. Alternatively, the template 21 can be curved so as to impart curved surfaces to the flaps 6 and 7 of the resulting mitral valve in their longitudinal, transverse or both directions. The degree of curvature of the template 21 in the longitudinal dimension is preferably the same as the curvature of a sphere having a radius equal to the length of the strut cord 13.

The actual relationships among the parameters of the first preferred embodiment, as reflected in the template 21 utilized to form the same are provided below.

Length of the base 23 of the anterior leaflet (33)=0.50×π×D (mm)

Length of the base 24 of the posterior leaflet (34)=0.50×π×D (mm)

Height of the Anterior Leaflet 25=0.51×d+10 (mm)

Height of the Posterior Leaflet 26=0.37×D+10 (mm)

Height of valve=D+17 (mm)

Commissural height 33a=D+5 (mm)

Distance between strut chords at base 22=0.4×D (mm)

Length of strut chord 13=1.08×D (mm)

Where D=diameter (mm) of the mitral valve prosthesis at its base

Figure 8:
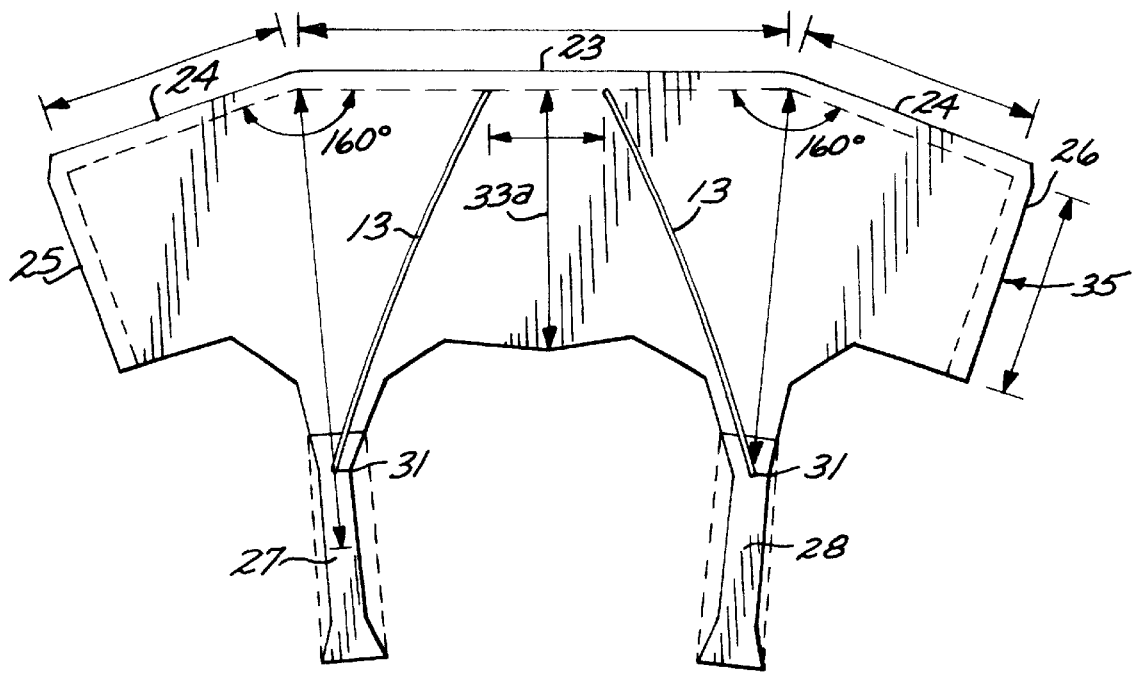
FIG. 8 is a top view of the second preferred embodiment of the template

FIG. 8 discloses another template 35 utilized to construct a second preferred embodiment of the mitral valve prosthesis of the present invention. This template 35 is similar in many aspects to the template 21 described above, and for this reason it needs to be described in lesser detail.

A substantial difference of template 35 from the template 21 is that instead of having flaps corresponding to the anterior 6 and posterior 7 leaflets in continuity, a flap or surface corresponding to the anterior leaflet 6 is situated in the middle of the template 35 and two flaps or surfaces that jointly correspond to the posterior leaflet 7 are located adjacent to the first flap. In the resulting mitral valve a suture 36 joining the two lateral sides of the membrane (corresponding to the two sides 25 and 26 of the template 35) is shorter than in the first embodiment and is located in the middle of the posterior leaflet 7. The suture 36 is shown in the perspective views of FIGS. 9 and 10 for both embodiments. The angles between the base 23 of the flap for the anterior leaflet 6 and the bases 24 of both halves of the flap for the posterior leaflet 7 are 160°, while the angles between the bases 24 of flaps for the posterior leaflet and the lateral sides 25 and 26, respectively, of the template 35 are approximately 90°. The relative sizes of the flaps for leaflets 6 and 7 of the extensions 27 and 28 corresponding to the chordal strips 15 and 16 and of the strut chords 13 are similar to the previously described embodiment and are provided below. The extremities of the extensions 27 and 28 for the chordal strips 15 and 16 are different than in the first preferred embodiment. In this embodiment they are formed of a straight strip approximately 22 mm in length and 10 mm in width with a slight widening at their ends. Again the shape of the chordal strips 15 and 16 of the second preferred embodiment is best illustrated by the template 36 that is used to form the membrane from which the prosthesis is made. In this embodiment the strips are folded approximately 10 mm from the points 31 of attachment of the strut chords 13 and sutured so that the end of the chordal strip has a double layer of pericardium. The areas corresponding to the sewing areas on the membrane are delineated by dotted lines on the template 21 and 35 of FIGS. 7 and 8.

The relationships among the parameters of the second preferred embodiment, as reflected in the template 35 utilized to form the same are provided below:

Length of the base 23 of the anterior leaflet 6=0.50×π×D (mm)

Length of the base 24 of the posterior leaflet 7=0.50×πD (mm)

Height of anterior leaflet 25=0.51×D+10 (mm)

Height of posterior leaflet 26=0.37×D+10 (mm)

Height of valve=D+15 (mm)

Commissural height 33a=D+5 (mm)

Distance between strut chords 13 at base (33)=0.4×D (mm)

Length of strut chords 13=1.15×D (mm)

Where D=diameter (mm) of mitral valve prosthesis at its base or prosthesis size.

Figure 9:
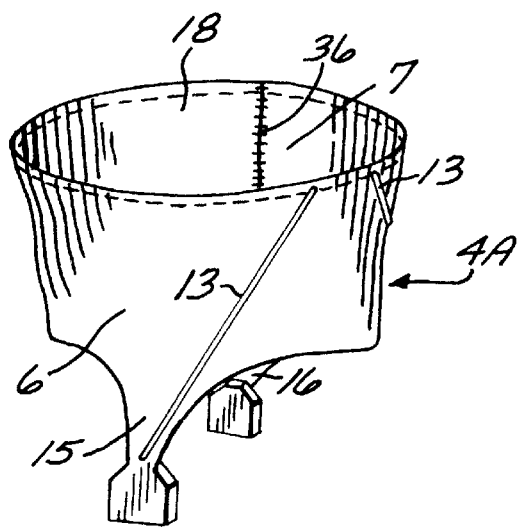
FIG. 9 is a perspective view of the first preferred embodiment of the mitral valve prosthesis of the present invention.
Figure 9A:
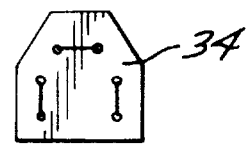
FIG. 9A is a plan view showing the suture points on a Teflon or like predget.

FIG. 9 is a perspective view of the first preferred embodiment of the mitral valve prosthesis 4A of the present invention. As it can be seen the lateral sides of the trimmed membrane have been joined together with a surgical suture 36 resulting in a two leaflet valve having a larger anterior 6 and a smaller posterior 7 leaflet. The diameter of the prosthesis is defined by the based 23 and 24 of the template 21. FIG. 9 also discloses the two chordal strips 15 and 16 of the valve. These are sutured to the anterior and posterior papillary muscles 10 and to one of the two strut chords 13. FIG. 9A discloses a preferred mode of placing sutures in the extremities of the chordal strips 15 and 16, affixing them to the anterior and posterior papillary muscles 10.

Figure 9B:
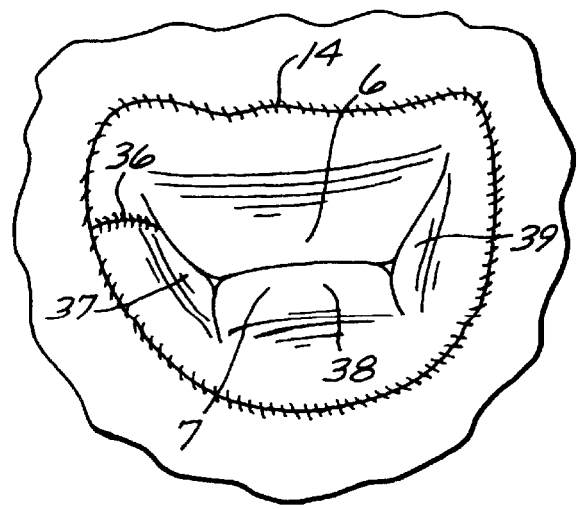
FIG. 9B is a perspective view of the first preferred embodiment, showing it in a closed position during systole.

The perspective view of FIG. 9B discloses and depicts the mitral valve prosthesis of the present invention as seen from the left atrium 5. The valve has been sutured in position with running sutures 14 between the base of the anterior leaflet 6 and the patient's mitral annulus 8 and the base of the posterior leaflet 7 to the patient's mitral annulus 8. The suture 36 between the two sides of the membrane to form a cone is shown. The valve is in the closed position showing a large anterior leaflet 6 and a posterior leaflet 7 with an appearance of three scallops 37, 38 and 39 similar to the appearance of a native mitral valve.

Figure 10:
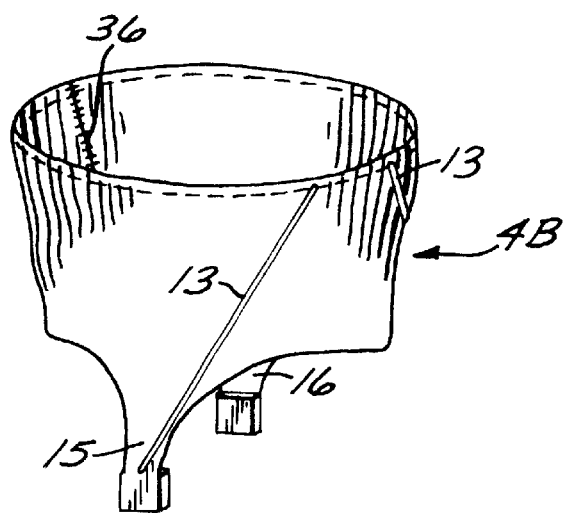
FIG. 10 is a perspective view of the second embodiment of the mitral valve prosthesis of the present invention.
Figure 10A:
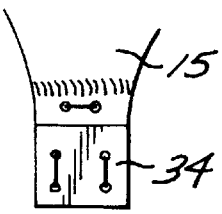
FIG. 10A is a plan view showing the suture points on a Teflon or like predget in accordance with the second preferred embodiment.

FIG. 10 is a perspective view of the second preferred embodiment of the mitral valve prosthesis of the present invention. As described above, this embodiment has been constructed with template 35. A principal difference from the first embodiment shown in FIG. 9 is that the suture 36 between the two lateral sides of the membrane corresponds to the midpoint of the posterior leaflet 7. FIG. 10A discloses a second preferred mode for placing sutures in the extremities of the chordal strips 15 and 16, affixing them to the anterior and posterior papillary muscles 10. Because the second preferred embodiment has a shorter suture 36 than the first, it is less likely to suffer dehiscence and is presently preferred.

Figure 10B:
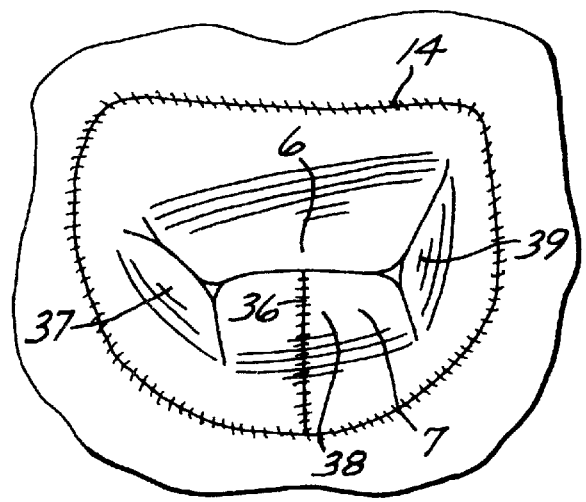
FIG. 10B is a perspective view of the second preferred embodiment showing it in a closed position during systole.

The perspective view of FIG. 10B is similar to FIG. 9B and discloses the second preferred embodiment in a closed position, as it is situated in systole. The suture 36 joining the two sides of the posterior leaflet 7 and three scallops 37, 38 and 39 of the posterior leaflet 7 which form when the mitral prosthesis of the present invention closes under pressure are visible in the figure.

Figure 11:
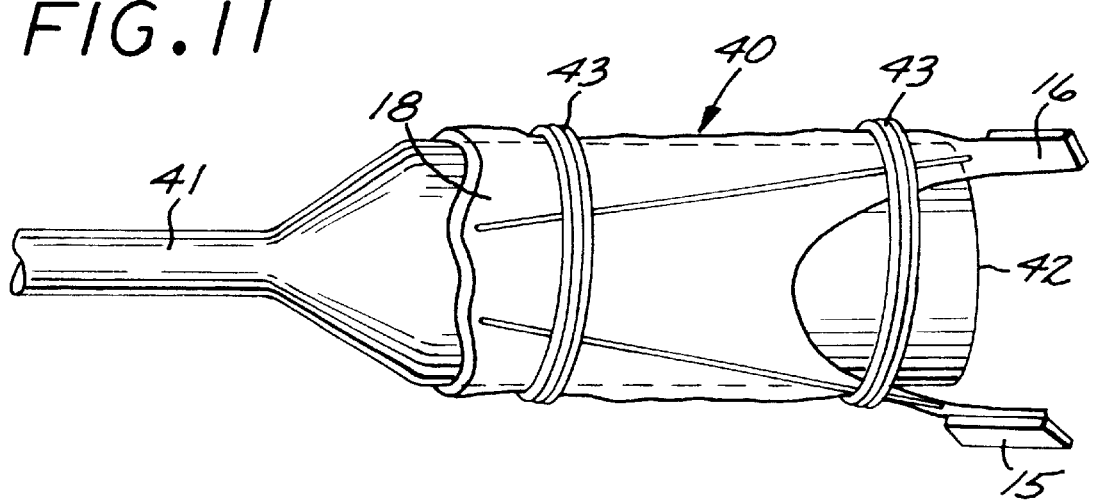
FIG. 11 is a perspective view of a holder in accordance with the present invention, the holder having the mitral valve prosthesis attached to it by bands.

FIG. 11 discloses a holder 40 to maintain the geometry of the mitral valve prosthesis of the present invention during its surgical insertion. Because the prosthesis is stentless, a rigid instrument is useful to hold the prosthesis while suturing its base 18 to the patient's mitral annulus 8 and the chordal strips 15 and 16 to the papillary muscles. The holder 40 is a rod of the appropriate diameter corresponding to the annulus or base 18 of the mitral prosthesis of the present invention. Each size of mitral valve prosthesis requires a specific sized holder. One end of the holder rod 40 terminates in a handle 41 to maintain the mitral valve prosthesis while the surgeon (not shown) sutures it to the patient. The other end 42 is rounded to avoid damage to the prosthesis. The holder 40 is introduced through the orifice of the mitral prosthesis so that the distal end of the prosthesis, corresponding to the extremity of the chordal strips 15 and 16, protrudes beyond the end 42 of the holder 40 and the base or upper end 18 of the mitral prosthesis is closer to the handle end 41 of the holder 40. In the preferred embodiment the mitral prosthesis is temporarily attached to the holder 40 with bands 43 situated close to the base 18 and close to the chordal strips 15 and 16. The bands 43, temporarily affixing the prosthesis to the holder 40 are made of materials well known in the art, such as polytetrafluorethylene (TEFLON®). In this fashion, the whole mitral valve of the present invention is held in position while the surgeon sutures the chordal strips 15 and 16 to the patient's papillary muscles 10. The bands 43 and the holder 40 are removed after the suturing is done, but before the suture 14 to the patient's mitral annulus is tied.

Figure 12:
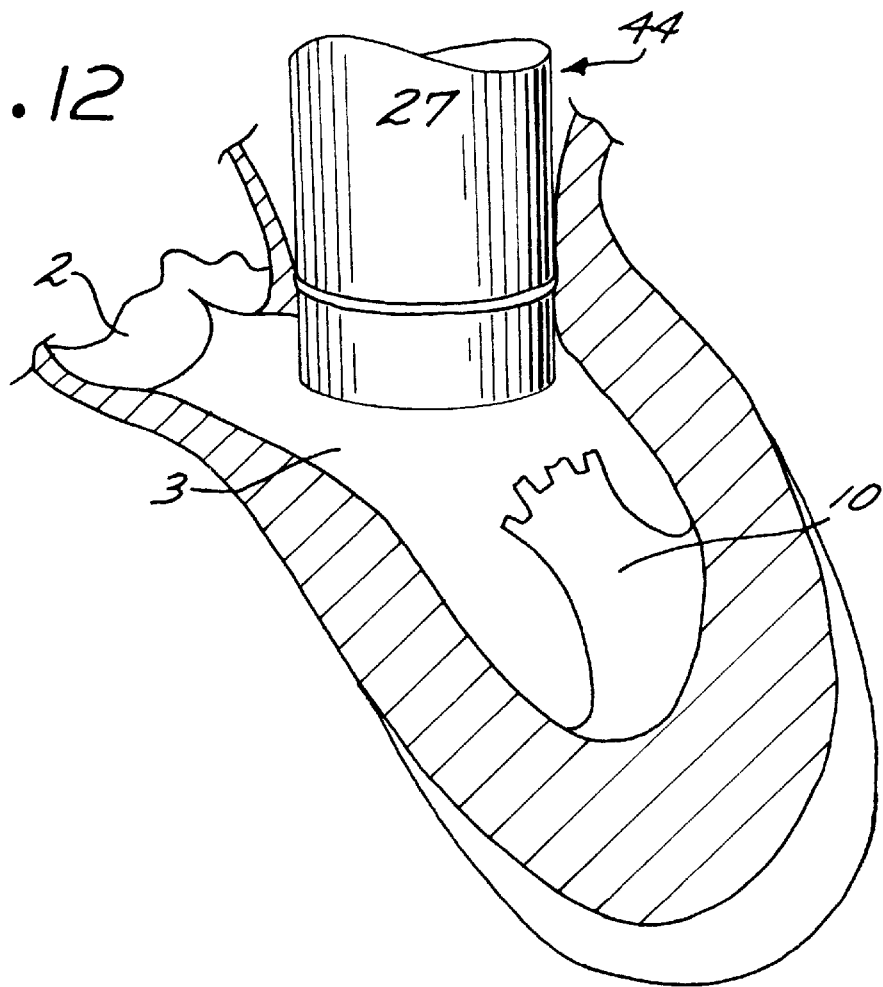
FIG. 12 is a schematic diagram, partly in cross-section, of the left ventricle showing a mitral valve sizer used to determine the diameter of the patient's mitral orifice.

FIG. 12 discloses an obturator and sizer 44 used to determine the diameter of the mitral orifice of the patient after his/her diseased mitral valve has been excised. The obturator 44 is also a rod similar to the mitral prosthesis holder 40 described in FIG. 11, but has no holding bands 43. A set of obturators 44 of varying diameters are constructed corresponding to the different diameters of the different patient's mitral orifices. Presently, obturators 44 of 25, 27, 29, and 31 mm diameter are contemplated as adequate for a wide range of patients. The obturator and sizer 44 is introduced through the open left atrium 5 then introduced through the mitral orifice of the patient to determine the diameter of the mitral orifice 8. Once the actual diameter of the patient's mitral orifice 8 has been determined, the appropriately sized mitral prosthesis of the present invention is selected. The obturator and sizer 44 is also used for another purpose, which is described below.

FIG. 12 depicts an obturator and sizer 44 marked "27", indicating for the surgeon that the diameter of this instrument is 27 mm.

Figure 13:
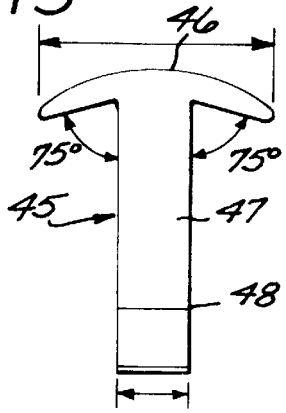
FIG. 13 is a plan view of an instrument designed to assist the surgeon to determine the location in the patient's papillary muscles where the chordal strips should be sutured.
Figure 13A:
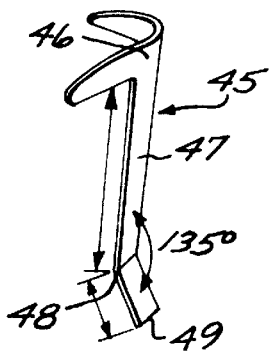
FIG. 13A is a perspective view of the instrument of FIG. 13.

FIGS. 13 and 13A disclose an instrument 45 designed to determine the appropriate location in the papillary muscles 10 of the patient where the chordal bands, 15 and 16 of the mitral prosthesis should be sutured. The instrument 45 is a convoluted endless wire loop that has a curved upper part 46 that is placed against the mitral annulus 8 of the patient at the level of the resected mid-scallop of the posterior leaflet. The length of the curved upper part 46 is approximately 1.2 of the diameter of the patient's mitral valve orifice (1.2×D). The curved portion 46 includes a downward extension 47 which is at an angle of 75° to the curved portion 46. The length of the first part of the extension 47 is approximately the measured diameter of the patient's mitral orifice. At that point, extension 47 bends at an angle of approximately 135° and extends further for approximately 10 mm where it turns at an angle of 90° to close the wire loop. The bend 48 of 135° angle indicates the most proximal location in the papillary muscle where the strut cords 13 are to be sutured to the chordal strips 15 and 16. The distal or bottom end 49 of the instrument 45 indicates to the surgeon (not shown) where the distal part of the chordal strips 15 and 16 should be sutured to the papillary muscles 10.

A set of instruments 45, having the aforesaid dimensions relative to differing annulus diameters (D) are provided within the scope of the invention.

Instead of being made of a loop of wire, the instrument 45 can also be made as a solid object, for example as a molded plastic object, that has substantially the same overall shape as the above-described loop of wire.

Figure 14:
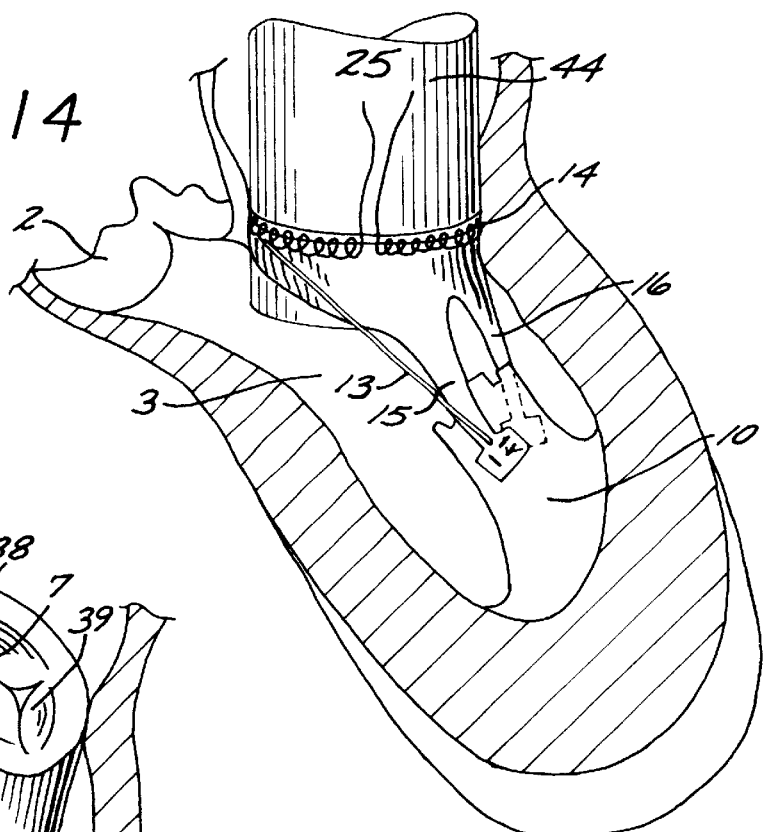
FIG. 14 is a schematic diagram, partly in cross-section, of the left ventricle, of the prosthesis of the invention and an obturator or mitral valve sizer of FIG. 12, used for avoiding constricting the mitral annulus when tying the sutures along the base of the prosthesis and the patient's annulus.

FIG. 14, similar to FIG. 4, is a diagram of the left heart cavities where the mitral prosthesis of the present invention has been placed within the left ventricle 3. The extremities of the chordal strips 15 and 16 of the mitral prosthesis have been anchored to the papillary muscles 10. The base 18 of the mitral prosthesis has been sutured 14 but not tied to the mitral orifice 8 of the patient, maintaining the strut chords 13 under tension. Because the prosthesis of the present invention is stentless, there is a danger of constricting the patient's mitral orifice 8 and the annulus or base 18 of the prosthesis when tying the sutures 14. This is avoided by using an obturator or sizer 44 of one size smaller than the measured size of the mitral prosthesis. This obturator 44 is introduced through the mitral orifice 8 and held while the sutures 14 are tied, thus eliminating the possibility of constricting the base 18 of the mitral prosthesis. The obturator and sizer 44 shown in FIG. 14 is marked "25", indicating that it is of 25 mm diameter, that is "one size smaller" than the obturator and sizer shown in FIG. 12.

Figure 15:
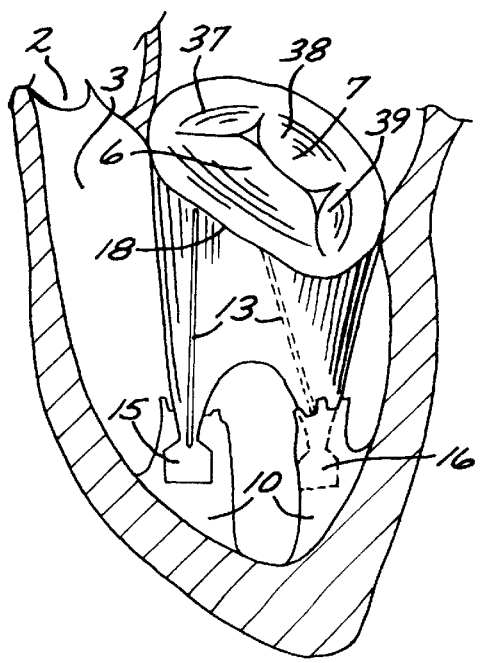
FIG. 15 is a schematic diagram showing the implanted mitral valve prosthesis during systole.

FIG. 15 discloses the mitral valve prosthesis of the present invention in place within the left ventricular cavity 3. The prosthesis is shown in the closed position and sutured at its base 18 to the mitral orifice 8 and its chordal strips 15 and 16 are sutured to the patient's papillary muscles 10. The two strut chords 13 extending from the papillary muscles 10 to the base 18 of the anterior leaflet 6 are also shown. Although the prosthesis only has one large anterior 6 and a smaller posterior 7 leaflet, when subjected to the left ventricular 3 systolic pressure, it acquires the shape of four leaflets: an anterior 6 and three scallops 37, 38 and 39, similar to the normal configuration of the natural mitral valve.

TEST RESULTS

The mitral valve prosthesis of the present invention is stentless because it does not incorporate any rigid structure and can therefore follow all the natural movements of the left ventricle. Its orifice adapts to the natural changes in size and shape of the patient's mitral orifice during the cardiac cycle. During diastole, when blood flows from the left atrium to the left ventricle, the mitral orifice and the prosthesis orifice both have a circular configuration achieving the maximum possible orifice area. During systole, the mitral orifice becomes smaller and "D" shaped, considerably reducing the orifice that has to be closed by the prosthesis.

The mitral valve prosthesis of the present invention is also anatomical because it imitates the general anatomical characteristics of the natural mitral valve. It has a large anterior and smaller posterior leaflets of trapezoidal shape made of a single flexible membrane that is anchored to the mitral orifice and maintained in position by the chordal strips of the same material which are anchored to the patient's papillary muscles. The prosthesis of the present invention like the natural valve also has two strut chords that maintain under constant tension the continuity between the mitral annulus and the papillary muscles.

Although the valve prosthesis of the invention has been described and is primarily used to replace a natural mitral valve, it could also be used, with only such modifications which may become readily apparent to those skilled in the art in light of the present disclosure, to replace a tricuspid valve.

The cardiac valve of the present invention can be assembled by the surgeon using a biocompatible membrane or the patient's own tissues such as pericardium. The patient's own pericardium is usually most readily available and is of low cost. However, it is preferred that the prosthesis be prepared in a specialized processing laboratory to assure quality control over the preparation, assembly and mounting of the prosthesis in its holder.

For testing the mitral prosthesis of the present invention has been constructed with porcine, bovine and sheep pericardium as described above. It has been tested both in vitro and in vivo.

In Vitro Test

In 10 isolated porcine hearts, the natural mitral valve was excised and the mitral prosthesis of the present invention was sutured in place as described above. The porcine hearts were then placed in a rig that injected saline into the left ventricular cavity at incremental pressures of 50, 100 and 150 mmHg while the atrial aspect of the prosthesis was continuously observed and still photographs taken. The amount of mitral regurgitation was measured at each pressure level. The two leaflets came in contact under left ventricular pressures below 50 mmHg and soon the posterior leaflet acquired a three scallop appearance similar to the natural valve shown in FIG. 15. The volume of mitral regurgitation measured was insignificant considering that the annular sutures were not yet healed. No regurgitant jets were observed, even at a left ventricular pressure of 200 mmHg.

In Vivo Tests

Mitral valve prosthesis of the present invention were tested in vivo by implantation into 8 adult sheep. Under general anesthesia and endotracheal anesthesia, a left thoracotomy of sheep through the fourth intercostal space was performed. A rectangle of pericardium from the sheep was resected and treated with 0.6% glutaraldehyde for ten minutes and then rinsed three times in saline for ten minutes. This treated autologous pericardium was then placed onto a template of the appropriate size (orifice diameters between 25 and 29 mm) and trimmed following the edges of the template. The two extremities of the pericardium were joined with a continuous 4/0 polypropylene suture. Two strut chords made of 3/0 polypropylene sutures were then anchored to the base of the prosthesis and to the extremity of the chordal strips. The extremities of the chordal strips were then sutured to 8×4 mm Teflon pledgets. The prosthesis so constructed was then placed into the prosthesis holder 38 shown in FIG. 11. During the time of construction of the mitral prosthesis, the sheep was placed under total cardiopulmonary by-pass with single cannulation of the right atrium and aorta. An apical left vent was placed into the left ventricle under continuous suction. The aorta was cross-clamped and 800 ml of crystalloid cardioplegia infused into the proximal ascending aorta. The left atrium was opened through the left appendage and the mitral valve orifice measured with the appropriate obturator and sizer 44, shown in FIG. 12. The sheep's mitral valve was completely excised. The mitral valve prosthesis of the present invention was then sutured in place, the atriotomy closed and the aortic clamp removed. The heart was defibrillated and the sheep weaned off by-pass. Simultaneous pressures were recorded from the left atrium and left ventricle. Epicardial echocardiograms were also performed and recorded. The chest was then closed and the animal placed in the recovery room under pain control medication. Four animals had a transthoracic echocardiographic study performed one week after surgery. All but one animal survived the surgery and were transported to the farm awaiting long-term studies. The one mortality (ID 949) resulted from the suture between the base of the prosthesis and the mitral annulus of the sheep dehiscing and creating a massive mitral insufficiency. This animal was the reason and origin for using an obturator in the mitral orifice before tying the annular sutures as shown in FIG. 14. The results of the implantations are in Tables 1–4.

As can be seen, the left atrial and left ventricular pressure were normal in all animals except the one that had the suture dehiscence. The mean trans-mitral gradients were very low. The echocardiographic studies showed very low mean trans-valvular gradients (1.7 mmHg) and a large mitral effective orifice area (5.21 $cm^2$). These data confirm the efficacy of the mitral valve prosthesis of the present invention.

TABLE 1

Hemodynamic data

| No. | ID | Weight (kg) | Sex | Valve Size | Heart Rate (beats/min) | Blood Pressure (mmHg) | LAP (mmHg) | LVP (mmHg) | Pressure gradient (mmHg) | |
|---|---|---|---|---|---|---|---|---|---|---|
| | | | | | | | | | Peak | Mean |
| 1 | 854 | 52 | F | 29 | 133 | 95/40 | 12/0 | 103/5 | 4 | 0 |
| 2 | 855 | 45 | M | 29 | 106 | 80/60 | 13/5 | 79/2 | 3 | 0 |
| 3 | 944 | 37 | F | 27 | 116 | 62/22 | 9/3 | 70/−1 | 8 | 3 |
| 4 | 912 | 37 | M | 27 | 116 | 82/39 | 20/10 | 82/7 | 7 | 2 |
| 5 | 929 | 46 | M | 29 | 117 | 80/34 | 21/9 | 112/5 | 8 | 2 |
| 6 | 949 | 31 | F | 25 | 106 | 87/33 | 30/6 | 86/6 | 3 | 0 |
| 7 | 917 | 41 | M | 27 | 125 | 82/47 | 7/1 | 84/1 | 3 | 0 |
| 8 | 951 | 44 | M | 27 | 115 | 83/47 | 13/4 | 96/3 | 7 | 1 |
| Mean | | 41.6 | | 27.5 | 116.8 | 81.4/40.2 | 15.6/4.8 | 89.0/3.5 | 5.4 | 1.0 |

LAP: Left Atrial Pressure
LVP: Left Ventricular Pressure

TABLE 2

Echocardiographic data (at operation day)

| No. | ID | Weight (kg) | Sex | Valve Size | Heart Rate (beats/min) | Blood Pressure (mmHg) | LVEDD (mm) | LVESD (mm) | EF (%) | Pressure Gradient (mmHg) | | EOA (cm²) | Grade of MR |
|---|---|---|---|---|---|---|---|---|---|---|---|---|---|
| | | | | | | | | | | Peak | Mean | | |
| 1 | 854 | 52 | F | 29 | 123 | 80/40 | 38.0 | 26.5 | 58.38 | 2.69 | 1 | 4.89 | 0 |
| 2 | 855 | 45 | M | 29 | 90 | 100/70 | 38.9 | 25.7 | 71.17 | | | | 0 |
| 3 | 944 | 37 | F | 27 | 102 | 108/48 | 34.9 | 23.4 | 62.55 | 5.02 | 3 | 5.37 | 0 |
| 4 | 912 | 37 | M | 27 | 96 | 90/45 | 35.6 | 24.8 | 58.72 | 1.00 | 0 | 5.37 | 0 |
| 5 | 929 | 46 | m | 29 | 103 | 87/46 | 34.0 | 22.2 | 65.06 | 5.11 | 1 | 5.95 | 0 |
| 6 | 949 | 31 | F | 25 | 114 | 95/40 | 39.4 | 24.1 | 69.86 | 9.12 | 3 | 4.15 | 2 |
| 7 | 917 | 41 | M | 27 | 120 | 88/44 | 37.5 | 24.5 | 64.65 | 5.20 | 2 | 5.24 | 0 |
| 8 | 951 | 44 | M | 27 | 102 | 92/48 | 38.7 | 26.2 | 61.25 | 7.18 | 2 | 5.50 | 0 |
| Mean | | 41.6 | | 27.5 | 106.2 | 92.5/47.6 | 37.1 | 24.7 | 63.95 | 5.05 | 1.7 | 5.21 | 0.3 |

LVEDD: Left Ventricular End Diastolic Diameter
LVESD: Left ventricular End Systolic Diameter
EF: Ejection Fraction
EOA: Effective Orifice Area

TABLE 3

Echocardiographic data (1 week post implantation)

| No. | ID | Sex | Valve Size | Heart Rate (beats/min) | Blood Pressure (mmHg) | LVEDD (mm) | LVESD (mm) | EF (%) | Pressure gradient (mmHg) | | EOA (cm²) | Grade of of MR |
|---|---|---|---|---|---|---|---|---|---|---|---|---|
| | | | | | | | | | Peak | Mean | | |
| 2 | 855 | M | 29 | 120 | 80/60 | 35.5 | 24.2 | 68.33 | 1.54 | 1 | 5.12 | 0 |
| 3 | 944 | F | 27 | 120 | Conscious | 36.9 | 26.0 | 57.41 | 3.76 | 1 | 5.50 | 0 |
| 4 | 912 | M | 27 | 114 | Conscious | 41.0 | 29.6 | 54.37 | 4.49 | 2 | 5.50 | 0 |
| 5 | 929 | M | 29 | 120 | Conscious | 38.2 | 22.9 | 71.44 | 9.36 | 3 | 5.95 | 0 |
| 7 | 917 | M | 27 | 94 | Conscious | 40.2 | 27.3 | 60.81 | 7.29 | 3 | 5.50 | 0 |
| Mean | | | 27.8 | 113.6 | | 38.4 | 26.0 | 62.47 | 5.29 | 2 | 5.51 | 0 |

LVEDD: Left Ventricular End Diastolic Diameter
LVESD: Left Ventricular End Systolic Diameter
EF: Ejection Fraction
EOA: Effective Orifice Area
MR: Mitral Regurgitation

TABLE 4

Echocardiographic data (1 week post implantation)

| No. | ID | Sex | Valve Size | Heart Rate (beats/min) | Blood Pressure (mmHg) | LVEDD (mm) | LVESD (mm) | EF (%) | Pressure gradient (mmHg) | | EOA (cm²) | Grade of of MR |
|---|---|---|---|---|---|---|---|---|---|---|---|---|
| | | | | | | | | | Peak | Mean | | |
| 4 | 912 | M | 27 | 102 | Conscious | 45.6 | 29.5 | 64.73 | 6.97 | 2 | 5.50 | 0 |
| 5 | 929 | M | 29 | 126 | Conscious | 37.7 | 22.6 | 71.48 | 4.75 | 2 | 5.79 | 0 |
| Mean | | | 28 | 114.0 | | 41.7 | 26.1 | 68.10 | 5.86 | 2.0 | 5.64 | 0 |

LVEDD: Left Ventricular End Diastolic Diameter
LVESD: Left Ventricular End Systolic Diameter
EF: Ejection Fraction
EOA: Effective Orifice Area
MR: Mitral Regurgitation

What is claimed is:

1. A stentless heart valve prosthesis to be used for the replacement of a diseased atrioventricular valve in the heart of a recipient mammal, comprising:

a single unitary body of biologically acceptable non-absorbable flexible membrane configured substantially in the shape of an anatomically correct mitral valve, the membrane forming a hollow inverted truncated cone having a substantially circular base forming an annulus at its first end, said base forming annulus corresponding to the mitral annulus of the heart of the recipient and configured and adapted for suturing into the mitral annulus of the heart of the recipient, the membrane further forming an anterior and posterior leaflet configured substantially in the form of the anterior and posterior leaflets of the natural mitral valve of the heart of the recipient, and the membrane still further forming two narrow extensions at its second end opposite to the annulus where the inverted cone is narrower than at its first end, the extensions substantially configured as anatomically correct cords and adapted to be sutured to the papillary muscle of the heart of the recipient, and two lines of biologically acceptable non-absorbable material, the lines configured and positioned as substantially anatomically correct strut cords of the natural mitral valve, each of said lines being affixed at one end substantially to the base of the truncated cone and at a second end substantially to the extremity of one of the extensions, respectively, whereby after implantation into the heart of the recipient the anterior and posterior leaflets of the prosthesis collapse during systole and form a plurality of scallops in substantial simulation of a natural mitral valve.

2. A heart valve prosthesis in accordance with claim 1 wherein each line configured as a strut cord is shorter than the total distance between the base of the prosthesis and the extremity of the respective extension.

3. A heart valve prosthesis in accordance with claim 1 wherein the membrane forming the truncated cone includes one suture along its length in the axial direction, the suture joining together the anterior and posterior leaflets.

4. A heart valve prosthesis in accordance with claim 3 wherein the membrane consists essentially of biocompatible synthetic material.

5. A heart valve prosthesis in accordance with claim 3 wherein the membrane consists essentially of biocompatible biological material.

6. A heart valve prosthesis in accordance with claim 5 wherein the biological material of the membrane is of autologous, homologous or heterologous origin.

7. A heart valve prosthesis in accordance with claim 1 wherein the membrane forming the truncated cone includes one suture along its length in the axial direction, the suture joining together two substantial halves of the posterior leaflet.

8. A heart valve prosthesis in accordance with claim 7 wherein the membrane consists essentially of biocompatible synthetic material.

9. A heart valve prosthesis in accordance with claim 7 wherein the membrane consists essentially of biocompatible biological material.

10. A heart valve prosthesis in accordance with claim 9 wherein the biological material of the membrane is of autologous, homologous or heterologous origin.

11. A heart valve prosthesis in accordance with claim 1 wherein a biologically acceptable reinforcing member is attached to the extremity of each one of the extensions whereby sutures attaching the extensions to the papillary muscle of the heart of the recipient have a reinforced base.

12. A stentless heart valve prosthesis to be used for the replacement of a diseased atrioventricular valve in the heart of a recipient mammal, comprising:

a single unitary body of biologically acceptable non-absorbable flexible membrane configured substantially in the shape of an anatomically correct mitral valve, the membrane forming a hollow inverted truncated cone having a substantially circular base forming an annulus at its first end, said base forming annulus corresponding to the mitral annulus of the heart of the recipient and configured and adapted for suturing into the mitral annulus of the heart of the recipient, the membrane further forming an anterior and posterior leaflet configured substantially in the form of the anterior and posterior leaflets of the natural mitral valve of the heart of the recipient, and the membrane still further forming two narrow extensions at its second end opposite to the annulus where the inverted cone is narrower than at its first end, the extensions substantially configured as anatomically correct cords and adapted to be sutured to the papillary muscle of the heart of the recipient, and two lines of biologically acceptable non-absorbable material, the lines configured and positioned as substantially anatomically correct strut cords of the natural mitral valve, each of said lines being affixed at one end substantially to the base of the truncated cone and at a second end substantially to the extremity of one of the extensions, respectively, and each line being shorter than the total distance between the base of the prosthesis and the extremity of the respective extension whereby after implantation into the heart of the recipient the anterior and posterior leaflets of the prosthesis collapse during systole and form a plurality of scallops in substantial simulation of a natural mitral valve.

13. A heart valve prosthesis in accordance with claim 12 wherein the membrane forming the truncated cone includes one suture along its length in the axial direction, the suture joining together the anterior and posterior leaflets.

14. A heart valve prosthesis in accordance with claim 13 wherein the membrane consists essentially of biocompatible biological material of autologous, homologous or heterologous origin.

15. A heart valve prosthesis in accordance with claim 14 wherein a biologically acceptable reinforcing member is attached to the extremity of each one of the extensions whereby sutures attaching the extensions to the papillary muscle of the heart of the recipient have a reinforced base.

16. A heart valve prosthesis in accordance with claim 12 wherein the membrane forming the truncated cone includes one suture along its length in the axial direction, the suture joining together two substantial halves of the posterior leaflet.

17. A heart valve prosthesis in accordance with claim 16 wherein the membrane consists essentially of biocompatible biological material of autologous, homologous or heterologous origin.

18. A heart valve prosthesis in accordance with claim 17 wherein the extremity of each of the extensions comprises a double layer of biological membrane whereby sutures attaching the extensions to the papillary muscle of the heart of the recipient have a reinforced base.

* * * * *